United States Patent [19]

Pala et al.

[11] 4,301,177
[45] Nov. 17, 1981

[54] (3-METHYL-2-BUTENYL)PROPANEDIOIC ACID MONO (1,2-DIPHENYLHYDRAZIDE) AND SALTS THEREOF

[75] Inventors: Gianfranco Pala, Milan; Enzo Cereda, Tortona, both of Italy

[73] Assignee: Istituto de Angeli S.p.A., Milan, Italy

[21] Appl. No.: 135,865

[22] Filed: Mar. 31, 1980

[30] Foreign Application Priority Data

Apr. 20, 1979 [DE] Fed. Rep. of Germany ....... 2915949

[51] Int. Cl.$^3$ ................. C07C 109/10; A01N 37/10
[52] U.S. Cl. .................................... 424/319; 562/439
[58] Field of Search ...................... 562/439; 424/319

[56] References Cited

U.S. PATENT DOCUMENTS 3,288,848 11/1966 Hinman et al. ................ 562/439
3,455,999 7/1969 Pfister et al. ................... 562/439

Primary Examiner—Natalie Trousof
Assistant Examiner—James H. Reamer
Attorney, Agent, or Firm—Hammond & Littell, Weissenberger & Muserlian

[57] ABSTRACT

The compound of the formula

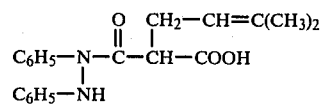

and non-toxic, pharmacologically acceptable salts thereof, which are useful as analgesics, antipyretics and anti-rheumatics.

4 Claims, No Drawings

(3-METHYL-2-BUTENYL)PROPANEDIOIC ACID MONO (1,2-DIPHENYLHYDRAZIDE) AND SALTS THEREOF

This invention relates to a novel derivative of N,N'-diphenylhydrazide and salts thereof, to methods of preparing these compounds, to pharmaceutical compositions containing them as active ingredients, and to methods of using them as analgesics, antipyretics and antirheumatics.

More particularly, the present invention relates to the novel compound (3-methyl-2-butenyl)propanedioic acid mono(1,2-diphenylhydrazide) of the formula

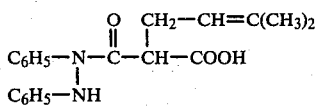

and non-toxic, pharmacologically acceptable salts thereof, especially the alkali metal and alkaline earth metal salts.

A particularly preferred salt is the calcium salt, in the form of its dihydrate, of the formula

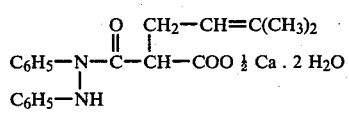

The compound of the formula I may be prepared by the following methods:

METHOD A

By alkaline hydrolysis of the known compound 4-(3-methyl-2-butenyl)-1,2-diphenyl-3,5-dioxo-pyrazolidine of the formula

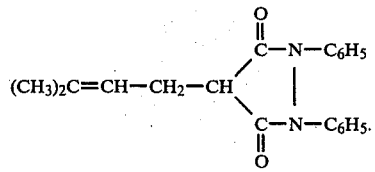

The hydrolysis is preferably carried out by dissolving the starting material of the formula II in a dilute alkali metal hydroxide, preferably sodium hydroxide, and heating the solution for a long time, for example, for 5 to 40 hours. The addition of an inorganic salt of sodium, for example sodium chloride, sodium acetate, or preferably disodium hydrogen phosphate, to the hydrolysis medium is of particular advantage in order to improve yields. The reaction product is then precipitated by adding an inorganic acid to the reaction medium. The precipitated acid is then converted, if desired, in conventional manner into the corresponding salt. For example, the sodium salt of the compound of the formula I is obtained by dissolving the acid monohydrazide of the formula I in ammonium hydroxide and precipitating the desired compound by the addition of a calcium salt, for example calcium chloride.

METHOD B

By alkaline hydrolysis of an ester of the formula

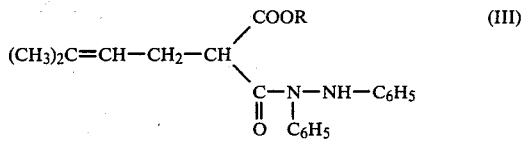

wherein R is lower alkyl, preferably ethyl.

The hydrolysis of the ester is carried out by heating a compound of the formula III with an alkali metal hydroxide solution, preferably a sodium hydroxide solution, and precipitating the acid monohydrazide by acidification with an inorganic acid. The conversion into a salt, particularly the calcium salt, is performed in conventional manner, for example by dissolving the acid monohydrazide in an alkali metal hydroxide, such as sodium hydroxide, and precipitating the desired salt. In this manner the calcium salt of the formula Ia can be precipitated by adding a salt of inorganic, soluble calcium salt such as calcium chloride.

The following examples illustrate the present invention and will enable others skilled in the art to understand it more completely. It should be understood, however, that the invention is not limited solely to the particular examples given below.

EXAMPLE 1

(3-Methyl-2-butenyl)propanedioic acid mono(1,2-diphenylhydrazide) and its calcium salt by method A 64 gm (0.2 mol) of 4-(3-methyl-2-butenyl)-1,2-diphenyl-3,5-dioxo-pyrazolidine were dissolved in an aqueous sodium hydroxide solution obtained by dissolving 16 gm (0.4 mol) of sodium hydroxide pellets in 640 ml of water. The solution was heated for 7 hours. The reaction mixture was then cooled to room temperature and washed twice with ether. The ether extract contained a little hydrazobenzene. The aqueous alkaline solution was then made acid to Congo red with 10% hydrochloric acid and quickly extracted with ethyl ether. The organic phase was evaporated to dryness, leaving (3-methyl-2-butenyl)propanedioic acid mono(1,2-diphenyl hydrazide) as an oily residue which was dissolved in a dilute ammonium hydroxide solution obtained by diluting 40 ml of an aqueous 32% ammonium hydroxide solution with 600 ml of water. To this solution was added a solution of 11 gm of calcium chloride in 40 ml of water. The calcium salt of (3-methyl-2-butenyl)-propanedioic acid mono(1,2-phenylhydrazide)dihydrate which precipitated upon stirring was suction filtered off and dried for 8 hours at 50° C. and 15 mmHg. The salt was obtained as a white solid. Yield: 54.06 gm (72% of theory), M.p. 166° C.

Analysis for $C_{40}H_{46}CaN_4O_8$: Calc.: C—63.98%; H—6.17%; Ca—5.33%; N—7.46%. Found: C—64.12%; H—6.08%; Ca—5.50%; N—7.57%.

EXAMPLE 2

(3-Methyl-2-butenyl)propanedioic acid mono(1,2-diphenylhydroazide) and its calcium salt by method A 103.8 gm (0.324 mol) of 4-(3-methyl-2-butenyl)-1,2-diphenyl-3,5-dioxopyrazolidine were dissolved in a solution of 12.96 gm (0.324 mol) of sodium hydroxide pellets and 57.3 gm (0.16 mol) of disodium hydrogen phosphate dodecahydrate in 400 ml of water. The reaction mixture was heated for 30 hours in an atmosphere of nitrogen, then cooled, diluted with 600 ml of water, and filtered. The filtered solution was neutralized (pH 7 to 7.5) with 2 N hydrochloric acid and extracted several times with chloroform. The combined chloroform extracts were evaporated, leaving crude 2-(3-methyl-2-butenyl)propanedioic acid mono(1,2-diphenylhydrazide) which was dissolved in 500 ml of 10% aqueous ammonium hydroxide. To this solution a solution of 17.9 gm (0.162 mol) of calcium chloride in 50 ml of water was added while stirring.

The calcium salt of 2-(3-methyl-2-butenyl)propanedioic acid mono(1,2-diphenylhydrazide) thus obtained was filtered off and dried for 8 hours at 50° C. and 15 mmHg.

This salt was obtained as a white solid (yield: 98.5 gm, 81% of theory) and had the same analytical and physico-chemical chracteristics as the end product of Example 1.

EXAMPLE 3

(3-Methyl-2-butenyl)propanedioic acid mono(1,2-diphenylhydrazide and its calcium salt by method B A suspension of 38.8 gm (0.105 mol) of the ethyl ester of (3-methyl-2-butenyl)-propanedioic acid mono(1,2-diphenylhydrazide) in 130 ml of aqueous 3.5% sodium hydroxide was refluxed for 22 hours. The solution was then cooled, washed twice with ethyl ether, and treated with decolorizing charcoal. The solution was made acid to Congo red with 5% acetic acid, and the oil which separated out was extracted with ethyl ether. The organic phase was washed with water until neutral, dried, and evaporated to dryness, leaving 23.1 gm of (3-methyl-2-butenyl)propanedioic acid mono(1,2-diphenyl hydrazide) as a colorless oil.

This product was converted into its calcium salt by dissolving it in 300 ml of 0.5 N sodium hydroxide and adding to this solution a solution of 3.78 gm (0.034 mol) of calcium chloride in 30 ml of water.

The calcium salt of (3-methyl-2-butenyl)propanedioic acid mono(1,2-diphenylhydrazide) which precipitated was filtered off and dried for 8 hours at 50° C. and 15 mm Hg. This salt was obtained as a white solid (Yield: 24 gm, 61% of theory overall) and had the same analytical and physico-chemical characteristics as the end product of Example 1.

The compound of the formula I and its alkali metal and alkaline earth metal salts, especially its calcium salt of the formula Ia, have useful pharmacodynamic properties. More particularly, they exhibit analgesic, anti-inflammatory and antipyretic activities in warm-blooded animals, such as mice and rats. The compounds of this invention are further characterized by low toxicity and a lack of adverse effects on the stomach, and are therefore useful for the treatment of rheumatic and other inflammatory disorders.

The above-indicated pharmacological properties of the compounds of the present invention were acertained and compared to those of the structurally most closely related known compound, butylpropanedioic acid mono(1,2-diphenylhydrazine) disclosed in U.S. Pat. No. 3,455,999 to Pfister et al., by the test methods described below, where A = Calcium salt of (3-methyl-2-butenyl)propanedioic acid mono(1,2-diphenylhydrazide), and B = Calcium salt of butylpropanedioic acid mono(1,2-diphenylhydrazide); generic name: Bumadizon calcium.

METHODS

In the present study the test compounds were administered perorally by means of a stomach tube as an aqueous suspension in 5% acacia gum at a constant volume of 10 ml/kg to male Swiss mice and male Sprague-Dawley rats. Control rats and mice were given a corresponding volume of the aqueous suspension medium. The results were statistically evaluated by Dunnett's test (C. V. Dunnett.: J.A. Stat. Ass., 40, 1096, 1955).

1. Anti-inflammatory activity

The anti-inflammatory activity was determined in the carrageenin edema test according to Winter et al., (see C. A. Winter, E. A. Risley, G. W. Muss: J. Pharm. Exp. Ther., 141, 369, 1963).

The edema was provoked in rats by a subplantar injection into the right hind paw of 0.1 ml of a 1% carrageenin suspension in sterile saline solution.

Rats were treated orally with the test compound 60 minutes before the injection of carrageenin. The volume of the foot was measured with a mercury differential volume-meter immediately before injection of the phlogistic agent, and 3 and 5 hours thereafter. The anti-inflammatory activity was evaluated as percent edema inhibition of treated rats in comparison with the controls, according to the following formula:

$$\frac{\text{edema volume (control rats)} - \text{edema volume (treated rats)}}{\text{edema volume (control rats)}} \times 100$$

The results obtained are shown in the following table:

TABLE I

| Anti-inflammatory activity (carrageenin-induced edema). | | | |
|---|---|---|---|
| Compound | Hours after carrageenin | Edema volume in mm$^3$ Mean ± standard deviation | |
| Controls | 3 | 1.50 ± 0.48 | (8) |
| | 5 | 2.28 ± 0.60 | (8) |
| A | 3 | 0.75** ± 0.32 | (7) Δ |
| 40 mg.kg | 5 | 1.37** ± 0.51 | (7) Δ |
| A | 3 | 0.94* ± 0.48 | (8) |
| 80 mg/kg | 5 | 1.48* ± 0.63 | (8) |
| A | 3 | 0.68** ± 0.16 | (8) |
| 160 mg/kg | 5 | 0.75** ± 0.42 | (8) |
| B | 3 | 1.42 ± 0.27 | (8) |
| 40 mg/kg | 5 | 2.06 ± 0.42 | (8) |
| B | 3 | 0.96* ± 0.39 | (8) |
| 80 mg/kg | 5 | 1.32** ± 0.60 | (8) |
| B | 3 | 0.87** ± 0.32 | (8) |
| 160 mg/kg | 5 | 1.25** ± 0.33 | (8) |

Δ 1 rat died during the test
*p<0.05 "Dunnett"-Test
**p<0.01
( ) = in parenthesis the number of rats.

2. Effect on arthritis induced in rats by Freund's adjuvant

Arthritis was induced in rats by intradermal injection of 0.1 ml of a heavy oil suspension containing 5 mg/ml of heat-killed *Mycobacteria tuberculosis* into the right hind foot pad. The following Mycobacteria strains were used: PN, DT and C. The severity of arthritis was evaluated by measuring the edema of the left paw (secondary lesion) by means of a mercury differential volume-meter. Animals showing at least 40% edema of the left hind paw on the 16th day were given orally 40, 80 or 160 mg/kg of the test compound from the 16th to the 20th day.

The paw edema was measured on the day of injection of Freund's adjuvant and on days 16 and 20.

The anti-inflammatory activity was evaluated as percent inhibition of edema in the treated rats in comparison with the controls, according to the following formula:

$$\frac{\text{edema volume (control rats)} - \text{edema volume (treated rats)}}{\text{edema volume (control rats)}} \times 100$$

The following table shows the results which were obtained:

TABLE II

Effect on arthritis induced by Freund's adjuvant.

| Compound | days | Edema volume in mm³ Mean ± standard deviation | % Inhibition |
|---|---|---|---|
| Controls | 20 | 2.88 ± 0.32 | (10) |
| A 40 mg/kg | 20 | 1.89** ± 0.36 | (8) 34 |
| A 80 mg/kg | 20 | 1.86** ± 0.35 | (8) 35 |
| A 160 mg/kg | 20 | 1.37** ± 0.49 | (8) 45 |
| B 40 mg/kg | 20 | 2.00* ± 0.37 | (8) 30 |
| B 80 mg/kg | 20 | 1.95** ± 0.65 | (8) 32 |
| B 160 mg/kg | 20 | 1.68** ± 0.58 | (8) 41.6 |

*p<0.05 "Dunnett"-Test
**p<0.01
( ) = in parenthesis the number of rats.

3. Analgesic activity

The analgesic activity was evaluated in mice by the hot plate test according to Janssen and Jageneau (J.Pharm.Pharmac., 9, 381, 1957).

The plate temperature was kept constant at 55° C.; the reaction time was determined before and 30, 60, 90 and 120 minutes after oral administration of the test compound. Average values after administration of the test compound were compared to those obtained before treatment.

The results obtained are shown in the following table:

TABLE III

Analgesic activity (hot plate-test): reaction time before and after administration of the test compound

| Compound | 0 | 30' | 60' | 90' | 120' |
|---|---|---|---|---|---|
| A 50 mg/kg | 15.40 ± 2.76 (10) | 16.70 ± 3.86 | 19.80** ± 3.36 | 20.00** ± 4.22 | 20.00** ± 1.76 |
| A 100 mg/kg | 12.90 ± 3.21 (10) | 16.30* ± 3.02 | 17.10* ± 5.26 | 16.90* ± 3.84 | 17.80* ± 4.26 |
| A 200 mg/kg | 14.40 ± 2.95 (10) | 19.90* ± 5.45 | 21.30** ± 4.79 | 20.10** ± 3.51 | 20.40** ± 5.83 |
| B 50 mg/kg | 14.00 ± 3.80 (10) | 16.50 ± 3.60 | 18.30* ± 3.06 | 19.30** ± 2.06 | 18.60* ± 4.12 |
| B 100 mg/kg | 14.30 ± 2.67 (10) | 17.50* ± 3.37 | 17.50* ± 3.87 | 17.10 ± 4.48 | 16.10 ± 2.56 |
| B 200 mg/kg | 12.90 ± 2.92 (10) | 16.89** ± 2.37 | 18.44** ± 2.51 | 17.22** ± 2.54 | 19.80** ± 3.14 |

*p<0.05
**p<0.01 "Dunnett"-Test
( ) = in parenthesis the number of rats.

4. Analgesic-anti-inflammatory activity

The analgesic-anti-inflammatory activity was evaluated in rats by the method of Randall and Selitto (Arch. Int. Pharmacodyn., 111, 409, 1957), using an analgesimeter to measure the minimum load that must be applied to a rat's hind paw to elicit a painful stimulus.

Both the controls and the experimental rats were injected into the right hind paw with 0.1 ml of 20% brewer's yeast in sterile saline immediately before the administration of the test compound.

The volume of the inflamed right hind paw was measured 1, 2 and 4 hours after the administration of the test compound.

The analgesic-anti-inflammatory activity was evaluated using an "analgesic index" expressed as a ratio between the sum of the average weights (grams) necessary to provoke a painful stimulus at different times in treated and control animals.

The results obtained are shown in the following table:

TABLE IV

Analgesic-anti-inflammatory activity
Mean of the weights (in grams) eliciting painful stimulus at different times and analgesic index.

| Compound | 1 h. | 2 h. | 4 h. | Analgesic Index |
|---|---|---|---|---|
| Controls | 116.2 | 87.6 | 78.8 | 1.0 |
| A (8) 40 mg/kg | 196.2 | 128.8 | 95.0 | 1.49 |
| A (8) 80 mg/kg | 192.6 | 147.6 | 146.2 | 1.72 |
| A (8) 160 mg/kg | 245.0 | 171.2 | 143.8 | 1.98 |
| B (8) 40 mg/kg | 145.0 | 108.8 | 105.0 | 1.27 |
| B (8) 80 mg/kg | 140 | 128.8 | 110.0 | 1.34 |
| B (8) 160 mg/kg | 142.8 | 161.2 | 140.0 | 1.57 |

( ) = in parenthesis the number of rats.

5. Antipyretic activity

The antipyretic activity was investigated in rats by the method of Niemegeers et al. (see Arzneim.Forsch. 25, 1519, 1975). The rectal temperature was measured immediately before and 4 hours after the subcutaneous injection of 1 ml/100 g body weight of a 15% brewer's yeast suspension in 1% acacia gum.

The test compound was administered orally to groups of 5 different rats per dose 4 hours after the yeast injection. The rectal temperature was measured 0.5, 1, 1.5, 2, 2.5, 3 and 19 hours after treatment.

Average values of the temperatures obtained in the treated rats were compared with those of control rats. The results obtained are shown in the following table:

The results obtained are shown in the following table:

TABLE V

Effect on fever induced by brewer's yeast in rats.

Rectal temperature (°C.) measured at different times (hours)
Mean ± standard deviation

| Compound | −4 | 0 | ½ | 1 | 1½ | 2 | 2½ | 3 | 19 |
|---|---|---|---|---|---|---|---|---|---|
| Controls | 37.21 | 38.16 | 38.28 | 38.22 | 38.22 | 38.13 | 38.13 | 38.03 | 37.36 |
|  | ±0.32 | ±0.11 | ±0.37 | ±0.41 | ±0.44 | ±0.36 | ±0.10 | ±0.13 | ±0.39 |
| A | 37.00 | 38.00 | 37.51** | 38.41 | 38.24 | 38.23 | 38.28 | 38.10 | 37.51 |
| 40 mg/kg | ±0.38 | ±0.31 | ±0.19 | ±0.55 | ±0.76 | ±0.74 | ±0.65 | ±0.57 | ±0.57 |
| A | 37.06 | 38.14 | 37.16** | 37.47* | 37.54* | 37.57* | 37.47* | 37.47* | 36.75* |
| 80 mg/kg | ±0.38 | ±0.46 | ±0.30 | ±0.56 | ±0.24 | ±0.31 | ±0.25 | ±0.17 | ±0.34 |
| A | 36.46 | 38.06 | 37.14** | 37.20** | 37.62* | 37.67* | 37.58** | 37.76* | 37.86* |
| 160 mg/kg | ±0.16 | ±0.25 | ±0.38 | ±0.37 | ±0.31 | ±0.28 | ±0.14 | ±0.20 | ±0.15 |
| B | 36.74 | 38.08 | 38.05 | 38.20 | 38.09 | 38.17 | 38.45 | 38.01 | 37.28 |
| 40 mg/kg | ±0.33 | ±0.37 | ±0.04 | ±0.66 | ±0.69 | ±0.78 | ±0.57 | ±0.45 | ±0.59 |
| B | 36.96 | 38.02 | 37.10** | 37.38** | 37.48** | 37.65 | 37.96 | 37.80 | 37.44 |
| 80 mg/kg | ±0.57 | ±0.47 | ±0.40 | ±0.30 | ±0.28 | ±0.80 | ±0.65 | ±0.71 | ±0.77 |
| B | 36.06 | 38.52 | 37.89 | 37.81 | 37.90 | 37.34** | 37.50 | 37.41** | 36.75* |
| 160 mg/kg | ±0.66 | ±0.23 | ±0.65 | ±0.48 | ±0.63 | ±0.26 | ±0.22 | ±0.08 | ±0.22 |

*$p<0.05$
**$p<0.01$ "Dunnett"-Test

6. Effect on normal temperature of rats

The rectal temperature was measured at 30-minute intervals before and after administration of the test compound, that is, at −1.5, −1, −0.5, 0.5, 1, 1.5 and 2 hours, using groups of 10 rats each for each dosage level.

Average values of the temperatures obtained in the treated rats were compared with those of control rats. The results obtained are shown in the following table:

TALBLE VI

Effect on the normal temperature of rats.

Rectal temperature (°C.) at different times (hours)
Mean ± Standard deviation

| Compounds | −1½ | −1 | −½ | ½ | 1 | 1½ | 2 |
|---|---|---|---|---|---|---|---|
| Controls | 37.13 | 36.73 | 36.36 | 36.33 | 36.62 | 36.68 | 36.57 |
|  | ±0.37 | ±0.58 | ±0.51 | ±0.41 | ±0.60 | ±0.73 | ±0.69 |
| A | 36.81 | 36.62 | 36.20 | 35.96 | 36.28 | 36.34 | 36.54 |
| 40 mg/kg | ±0.57 | ±0.76 | ±0.88 | ±0.77 | ±0.61 | ±0.50 | ±0.67 |
| A | 36.75 | 36.42 | 36.33 | 36.25 | 36.12 | 36.14 | 36.15 |
| 80 mg/kg | ±0.66 | ±0.46 | ±0.64 | ±0.45 | ±0.57 | ±0.61 | ±0.63 |
| A | 37.01 | 36.32 | 36.22 | 35.71** | 35.85** | 35.91** | 35.86** |
| 160 mg/kg | ±0.45 | ±0.76 | ±0.64 | ±0.27 | ±0.84 | ±0.37 | ±0.29 |
| B | 37.15 | 36.62 | 36.33 | 36.02 | 36.13 | 36.10 | 36.20 |
| 40 mg/kg | ±0.40 | ±0.70 | ±0.84 | ±0.95 | ±0.90 | ±0.91 | ±0.71 |
| B | 36.69 | 36.51 | 36.34 | 36.14 | 36.27 | 36.31 | 36.47 |
| 80 mg/kg | ±0.60 | ±0.57 | ±0.69 | ±0.72 | ±0.84 | ±0.64 | ±0.76 |
| B | 36.50 | 36.52 | 36.00 | 35.62** | 35.70** | 35.92* | 36.24 |
| 160 mg/kg | ±0.27 | ±0.59 | ±0.59 | ±0.58 | ±0.52 | ±0.88 | ±0.88 |

*$p<0.05$
**$p<0.01$ "Dennett"-Test

7. Acute toxicity

The acute toxicity was determined on groups of 10 rats treated orally with 500, 1000, 1500 and 2000 mg/kg of the test compound by means of a stomach tube.

The number of dead rats was recorded over 7 days after administration of the test compound, and LD$_{50}$ values were calculated according to Litchfield and Wilcoxon (J.Pharm. and Exp.Ther., 96, 99, 1949).

The results obtained are shown in the following table:

TABLE VII

LD$_{50}$ and confidence limits according to Litchfield and Wilcoxon. The values are expressed in mg/kg.

| A | B |
|---|---|
| 1,057.54 | 796.34 |
| 721.30–1550.51 | 537.75–1,179.28 |
| n = 40 | n = 40 | n = number of rats.

8. Ulcerogenic effect

The ulcerogenic effect was determined in rats by the method of Niemegeers et al. (Arzneimittel-Forschung 25, 1537, 1975). A single oral dose was administered to groups of 15 rats fasted for 9 hours before treatment and kept fasting throughout the whole experimental period. The animals were sacrificed 16 hours after treatment; the severity of lesions was scored according to an arbitrary scale ranging from + to + + + +. For each group of rats, an ulcerogenic index was calculated according to Pauls et al., (Gastroenterology 8, 774, 1947).

The results are shown in the following table:

TABLE VIII

Gastric lesions observed in rats.

| Compound | No. of animals | Body weight in grams Mean ± Standard Deviation | Mortality | % animals with gastric lesions | Ulcerogenic Index |
|---|---|---|---|---|---|
| Control | 15 | 191.67 ± 9.57 | 0 | 0 | 0 |
| 40 mg/kg A | 15 | 206.67 ± 9.00 | 0 | 0 | 0 |
| 80 mg/kg A | 15 | 205.33 ± 6.40 | 0 | 0 | 0 |
| 160 mg/kg A | 15 | 212.67 ± 12.23 | 0 | 0 | 0 |
| 320 mg/kg A | 15 | 218.67 ± 6.40 | 0 | 46.66 | 71.38 |
| 40 mg/kg B | 15 | 194.67 ± 7.43 | 0 | 0 | 0 |
| 80 mg/kg B | 15 | 190.67 ± 8.84 | 1 | 0 | 0 |
| 160 mg/kg B | 15 | 198.00 ± 11.46 | 0 | 6.66 | 0.47 |
| 320 mg/kg B | 15 | 186.67 ± 7.24 | 1 | 64.38 | 81.63 |

SUMMARY OF PHARMACOLOGY

The compound of the present invention exhibits anti-inflammatory (Table I), analgesic-anti-inflammatory (Table IV), and antipyretic (Table V) activities which are more effective than those of bumadizon calcium. It is to be noted that the antipyretic activity takes effect at a dosage which is still free from statistically significant hypothermic effect (Table VI). The analgesic activity of compound A in the hot plate test is higher, begins earlier and lasts longer than that of bumadizon calcium.

The effect on arthritis induced in rats by Freund's adjuvant is similar for both compounds.

In addition, compound A is less toxic (Table VII) and less ulcerogenic (Table VIII) than the prior art compound. It follows, therefore, that the properties of compound A, as compared with those of bumadizon calcium, represent on the whole a substantial therapeutical progress.

For pharmaceutical purposes the compounds of the present invention are administered to warm-blooded animals perorally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.28 to 14.23 mgm/kg body weight, preferably 0.71 to 7.2 mgm/kg body weight.

The following examples illustrate a few pharmaceutical dosage unit compositions comprising a compound of the present invention as an active ingredient and represent the best modes contemplated of using the invention. The parts are parts by weight unless otherwise specified.

EXAMPLE 4

Tablets

| Compound of the formula Ia | A | B | C |
|---|---|---|---|
| | 200 mg | 300 mg | 400 mg |
| Mycrocrystalline cellulose | 50 mg | 50 mg | 50 mg |
| Corn starch | 77 mg | 115 mg | 115 mg |
| Talcum and magnesium stearate | 3 mg | 5 mg | 5 mg |

EXAMPLE 5

Hard gelatine capsules

| Each capsule contains: | A | B | C |
|---|---|---|---|
| Compound of the formula Ia | 200 mg | 300 mg | 400 mg |
| Talcum | 5 mg | 5 mg | 5 mg |

EXAMPLE 6

Suppositories

| | A | B |
|---|---|---|
| Compound of the formula Ia | 300 mg | 400 mg. |
| Glycerides of fatty acids q.s. ad | 2 g | 2 g |

The compound of the formula I or another non-toxic, pharmacologically acceptable alkali metal or alkaline earth metal salt thereof may be substituted for the particular active ingredient in Examples 4 through 6. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The compound of the formula

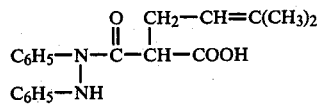

or a non-toxic, pharmacologically acceptable alkali metal or alkaline earth metal salt thereof.

2. The compound of claim 1, which is the calcium salt of (3-methyl-2-butenyl)propanedioic acid mono-(1,2-diphenylhydrazide).

3. An analgesic, antipyretic or antirheumatic pharmaceutical dosage unit composition consisting essentially of an inert pharmaceutical carrier and an effective analgesic, antipyretic or antirheumatic amount of a compound of claim 1.

4. The method of alleviating pain, reducing fever or relieving rheumatism in a warm-blooded animal in need thereof, which comprises perorally or rectally administering to said animal an effective analgesic, antipyretic, or antirheumatic amount of a compound of claim 1.

* * * * *